United States Patent
Linn et al.

(10) Patent No.: US 11,547,677 B2
(45) Date of Patent: Jan. 10, 2023

(54) TRANSMUCOSAL DELIVERY SYSTEM FOR IDEBENONE

(71) Applicants: LTS LOHMANN THERAPIE-SYSTEME AG, Andernach (DE); SANTHERA PHARMACEUTICALS (SCHWEIZ) AG, Prattein (CH)

(72) Inventors: Michael Linn, Waldbockelheim (DE); Markus Muller, Troisdorf (DE); Marius Bauer, Andernach (DE)

(73) Assignee: LTS LOHMANN THERAPIE-SYSTEME AG, Andernach (DE)

( * ) Notice: Subject to any disclaimer, the term of this patent is extended or adjusted under 35 U.S.C. 154(b) by 367 days.

(21) Appl. No.: 16/490,684

(22) PCT Filed: Feb. 28, 2018

(86) PCT No.: PCT/DE2018/100177
§ 371 (c)(1),
(2) Date: Sep. 3, 2019

(87) PCT Pub. No.: WO2018/157888
PCT Pub. Date: Sep. 7, 2018

(65) Prior Publication Data
US 2020/0009080 A1  Jan. 9, 2020

(30) Foreign Application Priority Data
Mar. 1, 2017 (DE) .......... 102017104277.6

(51) Int. Cl.
| | | |
|---|---|---|
| A61K 31/22 | (2006.01) |
| A61K 9/113 | (2006.01) |
| A61K 47/38 | (2006.01) |
| A61K 47/32 | (2006.01) |
| A61K 47/12 | (2006.01) |
| A61K 47/14 | (2017.01) |
| A61K 47/22 | (2006.01) |
| A61K 47/10 | (2017.01) |
| A61K 47/34 | (2017.01) |
| A61K 9/00 | (2006.01) |
| A61K 31/122 | (2006.01) |

(52) U.S. Cl.
CPC .......... *A61K 31/122* (2013.01); *A61K 9/006* (2013.01); *A61K 9/113* (2013.01); *A61K 47/10* (2013.01); *A61K 47/12* (2013.01); *A61K 47/14* (2013.01); *A61K 47/22* (2013.01); *A61K 47/32* (2013.01); *A61K 47/34* (2013.01); *A61K 47/38* (2013.01)

(58) Field of Classification Search
CPC ........ A61K 47/14; A61K 47/12; A61K 47/22; A61K 47/32; A61K 9/113; A61K 47/10; A61K 47/38; A61K 31/122; A61K 9/006; A61K 47/34; A61P 25/00
See application file for complete search history.

(56) References Cited

U.S. PATENT DOCUMENTS

| | | | |
|---|---|---|---|
| 2003/0235595 A1* | 12/2003 | Chen ...................... | A61K 9/107 514/571 |
| 2005/0281772 A1 | 12/2005 | Bromley et al. | |
| 2007/0190163 A1* | 8/2007 | Malaknov ................ | A61P 3/02 530/399 |
| 2009/0060993 A1 | 3/2009 | Schwarz et al. | |
| 2011/0281021 A1* | 11/2011 | Von Falkenhausen | ...... A61P 25/00 427/2.22 |
| 2014/0142076 A1 | 5/2014 | Ahmed et al. | |

FOREIGN PATENT DOCUMENTS

| | | | | |
|---|---|---|---|---|
| CN | 000102091038 B | 7/2012 | | |
| EP | 1891946 A1 | 2/2008 | | |
| EP | 2620141 A1 * | 7/2013 | ............ | A61K 9/006 |
| EP | 2620141 A1 | 7/2013 | | |
| WO | 2008019769 A1 | 2/2008 | | |
| WO | 2012129072 A1 | 9/2012 | | |
| WO | 2013107810 A1 | 7/2013 | | |
| WO | WO-2013107810 A1 * | 7/2013 | ............ | A61P 11/00 |
| WO | 2013110442 A1 | 8/2013 | | |

OTHER PUBLICATIONS

International Search Report for Application No. WO 2018/157888, dated Oct. 4, 2018, 6 pages.

* cited by examiner

*Primary Examiner* — Jianfeng Song
(74) *Attorney, Agent, or Firm* — Fay Sharpe, LLP

(57) ABSTRACT

The invention relates to a transmucosal delivery system for idebenone, comprising an external phase, which contains at least one hydrophilic polymer, and an inner hydrophobic phase, which contains idebenone and at least one hydrophobic substance, wherein the inner hydrophobic phase is emulsified in the form of droplets in the external phase. The invention is characterized in that the inner hydrophobic phase is stabilized by at least one emulsifier in the external phase. The invention also relates to a method for producing the same and its use as a medicament.

12 Claims, No Drawings

TRANSMUCOSAL DELIVERY SYSTEM FOR IDEBENONE

The present invention relates to a transmucosal delivery system for idebenone, to a method for the production thereof and to the use of such a system as a medicament.

Idebenone when administered orally is absorbed well in the gastrointestinal tract and is metabolised very quickly. It has been demonstrated that more than 98% idebenone is metabolised in the "first-pass metabolism". The metabolisation of idebenone in the liver leads to oxidation of the side chain of idebenone, reduction of the quinone ring, sulphate and glucuronide conjugation and subsequent renal excretion. The high liver metabolism in this case reduces the potentially high plasma levels of the pharmacologically active idebenone. Because of this high "first-pass metabolism", oral administration of idebenone requires high doses of the compound in order to attain pharmacologically effective plasma levels in the body. These high doses may lead to undesirable side-effects such as diarrhoea.

These problems can be addressed by administering idebenone by means of a transmucosal delivery system. Transmucosal delivery systems are thin polymer-based films containing active ingredient, which if applied to a mucous membrane, especially the oral mucosa, deliver the active ingredient directly into it. These administration systems have the advantage that the active ingredient is for the most part resorbed by the mucosa and thus the "first-pass metabolism", which has to be taken into account in the case of the conventional administration form of an active ingredient in tablet form, is avoided.

Administration of idebenone in the form of an oral film is known.

For instance, WO 2013/110442 A1 discloses the administration of idebenone as an oral film on the basis of a solid solution of idebenone in a water-soluble polymer.

WO 2013/107810 A1 discloses a transmucosal delivery system with a carrier material on the basis of a water-soluble polymer or a cellulose derivative.

WO 2008/0197691 A1 describes a transmucosal administration form for idebenone on the basis of a rapidly-dissolving tablet.

The administration forms for idebenone on the basis of an oral film made of water-soluble polymers known from the prior art have the disadvantage that idebenone is present in a solid solution or a suspension in a water-soluble polymer. As a highly hydrophobic compound, idebenone is present in solid solutions in a chemically and/or physically unstable state, which may result in the recrystallisation of idebenone. If idebenone is present in a suspension, this may have the disadvantage of reduced transmucosal resorbability. Aqueous suspensions of idebenone are furthermore difficult to produce owing to the low melting point of idebenone, since they can be dried only at very low temperatures without changing the physical properties of the active ingredient (e.g. particle size), and this, dependent on the layer thickness, results in very long drying times which cannot be implemented and are economically disadvantageous.

The aim of the present invention is to overcome the above-mentioned disadvantages of the prior art. Especially, the object of the present invention is to provide a transmucosal delivery system for idebenone wherein idebenone is present in a dissolved and chemically and physically stable state, which may also have a beneficial effect on transmucosal resorbability. In addition, the transmucosal delivery system should be simple and inexpensive to produce.

The above aim is addressed by a transmucosal delivery system for idebenone according to Claim 1 which comprises an outer, hydrophilic, phase which contains at least one hydrophilic polymer, and an inner, hydrophobic, phase which contains idebenone and at least one hydrophobic substance, wherein the inner, hydrophobic, phase is emulsified in the form of droplets in the outer, hydrophilic, phase, and wherein the transmucosal delivery system is characterised in that the inner, hydrophobic, phase is stabilised by at least one emulsifier in the outer, hydrophilic, phase.

The transmucosal delivery system for idebenone according to the invention is preferably present in the form of a liquid-in-solid dispersion.

The active ingredient is preferably dissolved in the inner, hydrophobic, phase which contains idebenone and at least one hydrophobic substance, which is preferably dispersed in droplet form in an outer, solid, phase based on a water-soluble polymer. To stabilise the emulsion, the transmucosal delivery system contains at least one emulsifier which stabilises the two phases with respect to phase separation.

Such a system has the advantage that idebenone can preferably be dissolved in the hydrophobic substance preferably in a concentration below its saturation concentration, which prevents the active ingredient from crystallising out. Although production of such a system is preferably water-based, in contrast to those systems in which idebenone is present in the form of a solid solution or suspension, a higher drying temperature can be selected since the active ingredient is present in solution and not in a solid form which is capable of melting. Thus acceptable drying times which make possible commercial, economically acceptable production of such a system are achieved.

"Idebenone" is understood to mean 2-(10-hydroxydecyl)-5,6-dimethoxy-3-methyl-cyclohexa-2,5-diene-1,4-dione, which is sold for example under the trade name Raxone® by Santhera Pharmaceuticals.

In a preferred embodiment of the transmucosal delivery system according to the invention, idebenone is present substantially in the inner, hydrophobic, phase of the system. "Substantially" is understood to mean that idebenone is present in the inner, hydrophobic, phase of the system to more than 80 wt. %, preferably more than 85 wt. %, and especially preferably more than 90 wt. %, relative to the total amount of idebenone in the system.

This has the advantage that idebenone is thus present substantially in a dissolved and hence chemically and/or physically stable state. If idebenone is present to less than 80 wt. % in the inner, hydrophobic, phase, this has the disadvantage that too much idebenone is present in the form of a solid solution or suspension in the outer, hydrophilic, phase, which can significantly adversely affect the transmucosal resorbability and the stability of the system and of the active ingredient.

In a preferred embodiment of the transmucosal delivery system according to the invention, idebenone is present dissolved substantially in non-crystalline form, preferably substantially in the inner, hydrophobic, phase.

"Substantially" is understood to mean that idebenone is present to more than 80%, preferably more than 85%, and especially preferably more than 90 wt. %, in non-crystalline form, and that this non-crystalline idebenone is present to more than 80 wt. %, preferably more than 85 wt. %, and especially preferably more than 90 wt. %, relative to the total amount of idebenone, in the inner, hydrophobic, phase of the system.

This has the advantage that idebenone is thus present dissolved substantially in non-crystalline form, which may result in better transmucosal resorbability.

If idebenone is present in non-crystalline form to less than 80 wt. %, this has the disadvantage that the transmucosal resorbability and the stability of the system and of the active ingredient is significantly adversely affected.

In a further preferred embodiment of the transmucosal delivery system according to the invention, idebenone is present in a pharmaceutically effective concentration below its saturation concentration, preferably substantially in the inner, hydrophobic, phase, preferably in a concentration which corresponds to 90%, preferably 95%, of the saturation concentration of idebenone in the inner, hydrophobic, phase. The expression "substantially" is understood here as defined above.

The saturation concentration of idebenone in the inner, hydrophobic, phase is dependent on the composition of the inner, hydrophobic, phase, but in a especially preferred embodiment amounts to from about 80 g/l to about 110 g/l at 4° C., preferably from about 90 g/l to about 105 g/l at 4° C., and from about 120 g/l to about 155 g/l at room temperature, preferably from about 130 g/l to about 150 g/l at room temperature. The saturation concentration in this case is determined as follows:

Idebenone is added in excess to the inner, hydrophobic, phase, so that even after relatively long stirring solid dregs of active ingredient are still present. Then the dregs are removed by centrifuging. The resulting supernatant contains idebenone in its saturation concentration. This is determined by analysis for example by means of HPLC.

If idebenone is present in a concentration below its saturation concentration, this has the advantage that recrystallisation of idebenone can be largely prevented, which may result in significantly better transmucosal resorbability and improved stability of the active ingredient and the system.

The outer, hydrophilic, phase of the transmucosal delivery system according to the invention comprises at least one hydrophilic polymer. A hydrophilic polymer is a polymer which contains polar and/or charged groups which make the polymer water-soluble.

These hydrophilic polymers may be selected from the group consisting of starch and derivatives thereof, agar-agar, gelatine and other gel-forming proteins, cellulose and derivatives thereof, alginic acid, galactomannan, carrageen and other vegetable gums, pullulan, xanthan gum, pectin and other glucans, dextran, polyvinylpyrrolidone, polyvinyl alcohol, poly(meth)acrylates, polyalkylene glycols, carboxyvinyl polymers and/or copolymers thereof.

In a preferred embodiment, the at least one hydrophilic polymer comprises polyvinyl alcohol, polyvinylpyrrolidone, a cellulose derivative and/or copolymers thereof.

These hydrophilic polymers have the advantage that when dried they form a thin stable film which when applied to the mucosa breaks up within a pharmaceutically acceptable timeframe and thus releases the active ingredient. This has the advantage of relatively rapid availability of the active ingredient and also of residue-free administration of the active ingredient.

The inner, hydrophobic, phase of the transmucosal delivery system according to the invention comprises at least one hydrophobic substance. Advantageously, the hydrophobic substance is selected from the group of pharmaceutically acceptable hydrophobic substances, such as isopropyl myristate, isopropyl palmitate, isopropyl stearate, isopropyl oleate, n-butyl stearate, n-hexyl laurate, n-decyl oleate, isooctyl stearate, isononyl stearate, isononyl isonanoate, 2-ethylhexyl palmitate, 2-ethylhexyl laurate, 2-hexyldecyl stearate, dialkyl ethers, alcohols, fatty acid triglycerides, such as triglycerol esters of saturated and/or unsaturated alkanecarboxylic acids, synthetic, semisynthetic and natural oils, such as olive oil, almond oil, avocado oil, sunflower oil, soybean oil, peanut oil, rapeseed oil, palm oil, coconut oil, palm kernel oil, 2-octyldodecyl palmitate, ethyl oleate, oleyl oleate, oleyl ecurate, erucyl oleate and also synthetic, semi-synthetic and natural mixtures of such esters, paraffin oil, squalene or squalane, fatty alcohols with 6 to 18 carbon atoms in straight chains and/or acids from the group laurylic acid, palmitic acid, myristic acid, aradidone, oleic acid, linolenic acid and linoleic acid, methyl salicylate, tributyl citrate, triethyl citrate, eucalyptol, 1,2-propanediol and/or methyl salicylate.

In a preferred embodiment, the at least one hydrophobic substance in the inner, hydrophobic, phase has a log P value of greater than 1, preferably of greater than 1.5, especially preferably of greater than 2.

The n-octanol/water partition coefficient $K_{ow}$ (notations such as "octanol/water partition coefficient" are also customary and correct) is a dimensionless partition coefficient known to the person skilled in the art which indicates the ratio of the concentrations of a chemical in a two-phase system consisting of n-octanol and water, and hence is a measurement of the hydrophobicity or hydrophilicity of a substance. The log P value is the common logarithm of the n-octanol/water partition coefficient $K_{ow}$. In such case:

$$K_{ow} = P = \frac{c_o^{Si}}{c_w^{Si}} \text{ and}$$

$$\log P = \log \frac{c_o^{Si}}{c_w^{Si}} = \log c_o^{Si} - c_w^{Si}$$

with $C_o^{Si}$=concentration of a chemical in the octanol-rich phase and
$C_w^{Si}$=concentration of a chemical in the water-rich phase.

$K_{ow}$ is greater than one if a substance is better soluble in fat-like solvents such as n-octanol, less than one if it is better soluble in water. Correspondingly, log P is positive for lipophilic and negative for hydrophilic substances. Since idebenone is a very hydrophobic substance, idebenone preferably dissolves in a hydrophobic substance with a log P value of greater than 1, preferably of greater than 1.5, especially preferably of greater than 2. In substances with a negative log P value, idebenone is present merely in the form of a suspension or in crystalline form, which as stated above is not preferable.

In a preferred embodiment, the at least one hydrophobic substance in the inner, hydrophobic, phase comprises tributyl citrate, triethyl citrate, eucalyptol, 1,2-propanediol, methyl salicylate, linoleic acid, oleic acid and/or mixtures thereof, but is not limited to these.

The transmucosal delivery system according to the invention comprises at least one emulsifier. "Emulsifier" is a designation of auxiliaries for producing and stabilising emulsions which in a narrower sense can also be referred to as surface-active agents or surfactants and as a rule are present as oily to wax-like, but also powdered, substances. To stabilise emulsions over a relatively long timeframe, auxiliaries which prevent the segregation of the two phases oil and water to the thermodynamically stable final state or delay it until the emulsion has served its purpose are required. This can be achieved by stabilisers and/or emulsifiers.

Examples of emulsifiers are soaps, metal soaps, organic soaps, such as ethanolamine oleates or stearates, sulphonated compounds, such as sodium dodecyl sulphate, quaternary ammonium compounds, fatty alcohols, such as lauryl alcohol, cetyl alcohol, stearyl alcohol or palmityl alcohol, partial fatty acid esters of polyhydric alcohols with saturated fatty acids, such as glycerol monostearate, pentaerythritol monostearate, ethylene glycol monostearate, propylene glycol monostearate, partial fatty acid esters of polyhydric alcohols with unsaturated fatty acids, such as glycerol monooleate, pentaerythritol monooleate, further polyoxyethylene esters of fatty acids, such as polyoxyethylene stearate, polymerisation products of ethylene oxide and propylene oxide with fatty alcohols, such as fatty alcohol polyglycol ethers or fatty acids, such as fatty acid ethoxylates, polysorbates, sorbitan esters, mono- or diglycerides and/or polyoxyethylene fatty acid ethers.

Emulsifiers can be characterised by the HLB value (HLB=hydrophilic-lipophilic balance=hydro-lipophilic ratio). The HLB value is a measurement of the solubility in water or in oil of predominantly non-ionic surfactants and the stability of emulsions.

The HLB value for non-ionic surfactants can be calculated as follows $$HLB = 20 \times \left(1 - \frac{M_l}{M}\right),$$

wherein $M_l$ is the molecular weight of the lipophilic content of a molecule and M is the molecular weight of the entire molecule. The factor 20 is a freely selected scaling factor. A scale of 0 to 20 thus results. An HLB value of 1 is indicative of a lipophilic compound: a chemical compound with an HLB value of 20 has a high hydrophilic content. A value of between 3 and 8 is assigned to water-in-oil emulsifiers, and a value of between 8 and 18 to oil-in-water emulsifiers.

In a preferred embodiment, the transmucosal delivery system is characterised in that the at least one emulsifier has an HLB value of 3 to 15. Emulsifiers having an HLB value in this range are especially well suited for stabilising the inner, hydrophobic, phase containing idebenone, in the outer, hydrophilic, phase containing at least one hydrophilic polymer. Emulsifiers having HLB values of more than 15 or less than 3 have the disadvantage that they do not form a stable emulsion, and thus lead to unstable transmucosal administration systems for idebenone.

In a preferred embodiment, the at least one emulsifier comprises polysorbates, sorbitan esters and/or polyoxyethylene fatty acid ethers or mixtures thereof, such as are known for example under the trade names Polysorbate 80, Span 83 or 85 and Brij S2, but is not restricted to these.

Furthermore, it is preferred for the transmucosal delivery system according to the invention additionally to comprise at least one free-radical scavenger and/or an antioxidant. The at least one free-radical scavenger and/or antioxidant is a chemical compound which prevents or reduces undesirable oxidation of other substances, specifically the active ingredient, and thus counteracts ageing of the transmucosal delivery system. Specifically, free-radical scavengers and/or antioxidants are distinguished in that they prevent the oxidative degradation, caused by atmospheric oxygen, of sensitive molecules, here specifically the active ingredient which is contained.

It is especially preferred for the at least one free-radical scavenger to be vitamin B.

The at least one free-radical scavenger and/or the antioxidant is preferably contained in the transmucosal delivery system in an amount of from about 0.05 to about 0.2 wt. %, and preferably from about 0.1 to about 0.2 wt. %, relative to the total weight of the transmucosal delivery system.

Furthermore, the transmucosal delivery system according to the invention may contain additional additives known to the person skilled in the art. These additives comprise flavourings, colourings, taste-masking substances, permeation enhancers, sweeteners, fillers, liquid, preferably lipophilic, auxiliaries and/or pH stabilisers.

Furthermore, it is preferred for the inner, hydrophobic, phase of the transmucosal delivery system according to the invention to make up about 30 to about 60 wt. %, and preferably about 40 to about 50 wt. %, relative to the total weight of the transmucosal delivery system.

If the amount of about 60 wt. % is exceeded, this has the disadvantage that a homogeneous emulsion can no longer be produced. If the amount falls short of about 30 wt. %, the necessary amount of active ingredient can no longer be accommodated in the transmucosal delivery system according to the invention.

Furthermore, it is preferred for the outer, hydrophilic, phase of the transmucosal delivery system according to the invention to make up about 20 to about 70 wt. %, preferably about 30 to about 40 wt. %, relative to the total weight of the transmucosal delivery system.

If the amount of about 70 wt. % is exceeded, this has the disadvantage that a homogeneous emulsion can no longer be produced.

If the amount falls short of about 20 wt. %, this has the disadvantage that the necessary amount of active ingredient can no longer be accommodated in the transmucosal delivery system according to the invention.

Furthermore, it is preferred for the emulsifier to make up about 2 to about 7 wt. %, and preferably about 3 to about 6.5 wt. %, relative to the total weight of the transmucosal delivery system according to the invention.

If the amount of about 7 wt. % is exceeded, this has the disadvantage that the emulsion undergoes a physical change.

If the amount falls short of about 2 wt. %, this has the disadvantage that the hydrophobic phase cannot be stabilised in the hydrophilic phase.

The transmucosal delivery system for idebenone according to the invention has a surface area of about 0.5 $cm^2$ to about 10 $cm^2$, preferably of about 2 $cm^2$ to about 8 $cm^2$.

In this case, the transmucosal delivery system according to the invention has a weight per unit area of about 50 $g/m^2$ to about 250 $g/m^2$, preferably of about 75 $g/m^2$ to about 225 $g/m^2$.

This corresponds to a layer thickness of about 20 μm to about 500 μm, preferably of about 50 μm to about 300 μm.

The transmucosal delivery system for idebenone according to the invention dissolves in the oral cavity preferably within a timeframe of less than about 30 min, more preferably within a timeframe of less than about 15 min, and very especially preferably within a timeframe of less than about 10 min.

The present invention further relates to a method for producing the transmucosal delivery system for idebenone according to the invention. The method comprises the steps:
a1) producing an aqueous solution, comprising the at least one hydrophilic polymer;
a2) producing a second solution, comprising idebenone and the at least one hydrophobic substance,
wherein at least one of the two solutions of steps a1) or a2) additionally comprises the at least one emulsifier, b) mixing the two solutions from steps a1) and a2) in order to obtain an emulsion; and c) spreading out and drying the emulsion obtained in step b) so that the dried emulsion has a weight per unit area of about 50 to about 250 g/m².

The present invention further relates to a transmucosal delivery system for idebenone obtainable according to the method described above.

Finally, the present invention relates to the transmucosal delivery systems for idebenone described in greater detail above and to the transmucosal delivery systems for idebenone obtainable according to the method described above as a medicament.

Further, the present invention relates to a transmucosal delivery system for idebenone in the treatment of Friedreich's ataxia, Duchenne muscular dystrophy, primary progressive multiple sclerosis, Leber's hereditary optic neuropathy.

The invention will be discussed below with reference to non-limitative examples.

EXAMPLE 1

The examples according to the invention 45, 47, 48, 53, 58 to 61 and 75 to 78 all form a physically and chemically stable emulsion. Comparison example 38, which does not contain any emulsifier or any hydrophobic substance, does not form an emulsion. Comparison examples 49 to 51, which do not contain any emulsifier, are either non-homogeneous or exhibit physical changes. Comparison example 52 exhibits slight inhomogeneity, since it does not contain enough emulsifier. Comparison examples 54, 56 and 57 are non-homogeneous, since they do not contain any hydrophobic substance. Comparison example 64 contains the emulsifier ATMOS 300 which is not according to the invention, the use of which leads to a non-homogeneous emulsion.

EXAMPLE 2

The saturation concentration of idebenone for an exemplified composition according to the invention was determined as follows.

Idebenone is added in excess to the inner, hydrophobic, phase, so that even after relatively long stirring solid dregs of active ingredient are still present. Then the dregs are removed by centrifuging. The resulting supernatant contains

|  |  |  |  | Inner, hydrophobic, phase | | | | |  |
|---|---|---|---|---|---|---|---|---|---|
| Sample | PVA 4-88 [%] | Emulsifier [%] | HLB value of the emulsifier | MS [%] LogP = 2.24 | DMI [%] LogP = −0.6 | TBC [%] LogP = 4.7 | EUC [%] LogP = 2.8 | Other [%] | Evaluation |
| 38 | 39.90 | — |  | — | 25.00 | 25.00 | — | 0.10 vitamin E | No emulsion |
| 45 | 38.80 | 4.74 PS80 | 15.0 | 47.46 | — | — | — | 0.11 vitamin E | Good |
| 46 | 39.77 | — |  | — | 5.05 | 25.08 | — | 0.11 vitamin E | Physical change |
| 47 | 38.32 | 4.19 PS80 | 15.0 | 23.86 | — | — | 23.93 | 0.14 vitamin E | Good |
| 48 | 37.92 | 5.31 PS80 | 15.0 | 23.86 | — | 23.58 | — | 0.12 vitamin E | Good |
| 49 | 39.95 | — |  | — | 49.93 | — | — | 0.13 vitamin E | Non-homogeneous |
| 50 | 39.59 | — |  | — | 24.73 | — | 24.65 | 0.12 vitamin E | Physical change |
| 51 | 39.89 | — |  | — | 27.97 | 25.02 | — | 0.11 vitamin E | Physical change |
| 52 | 39.55 | 1.97 PS80 | 15.0 | — | — | — | 48.56 | 0.15 vitamin E | Slightly non-homogeneous |
| 53 | 39.42 | 5.45 PS80 | 15.0 | — | — | 22.92 | 22.94 | 0.10 vitamin E | Good |
| 54 | 37.34 | 6.79 PS80 | 15.0 | — | — | 46.43 | — | 0.11 vitamin E | Non-homogeneous |
| 55 | 37.50 | 5.00 PS80 | 15.0 | 47.40 | — | — | — | 0.10 vitamin E | Good |
| 56 | 36.40 | 8.00 PS80 | 15.0 | — | — | 45.50 | — | 0.10 vitamin E | Physical change |
| 57 | 39.50 | 1.00 PS80 | 15.0 | — | 49.40 | — | — | 0.10 vitamin E | Non-homogeneous |
| 58 | 36.90 | 5.00 PS80 | 15.0 | 24.00 | — | — | 24.00 | 0.10 vitamin E | Good |
| 59 | 35.90 | 6.00 PS80 | 15.0 | 24.00 | — | 24.00 | — | 0.10 vitamin E | Good |
| 60 | 39.60 | 6.00 PS80 | 15.0 | 14.00 | — | 19.00 | 14.00 | 0.10 vitamin E | Good |
| 61 | 35.90 | 6.00 PS80 | 15.0 | 14.00 | 5.00 | 15.00 | 14.00 | 0.10 vitamin E | Good |
| 64 | 32.10 | 6.00 Atmos 300 6.00 PS80 | 2.5 15.0 | 13.00 | — | 10.00 | 13.00 | 0.10 vitamin E 0.10 vit. E. TPGS 4.50 sucralose 0.20 patent blue | Non-homogeneous |
| 75 | 36.90 | 6.00 PS80 | 15.0 | 10.00 | — | 19.00 | 18.00 | 0.10 vitamin E | Good |
| 76 | 36.90 | 6.00 Brij S2 | 4.90 | 10.00 | — | 19.00 | 18.00 | 0.10 vitamin E | Good |
| 77 | 36.90 | 4.00 PS80 2.00 Brij S2 | 15.0 4.9 | 10.00 | — | 19.00 | 18.00 | 0.10 vitamin E | Good |
| 78 | 37.40 | 3.50 PS80 1.50 Brij S2 | 15.0 4.90 | 9.00 | — | 17.00 | 16.00 | 0.10 vitamin E 1.00 lemon lime 1.00 peppermint 1.50 sucralose | Good |
| 79 | 37.00 | 3.50 PS80 1.50 Brij S2 | 15.0 4.90 | 9.00 | — | 15.00 | 14.40 | 0.10 vitamin E 5.00 spearmint 3.00 mask flavour 1.50 sucralose | Good |

PVA 4-88: polyvinyl alcohol (outer, hydrophilic, phase)
PS80: Polysorbate 80
MS: methyl salicylate
TBC: tributyl citrate
EUC: eucalyptol
DMI: dimethyl isosorbide
Atmos 300: mono- and diglycerides idebenone in its saturation concentration. This is determined by analysis for example by means of HPLC.

| Amount [wt. %] | Ingredient |
|---|---|
| 0.17 | vitamin E |
| 6.74 | Polysorbate 80 |

| Amount [wt. %] | Ingredient |
| --- | --- |
| 19.29 | methyl salicylate |
| 34.46 | eucalyptol |
| 36.44 | tributyl citrate |
| 2.89 | Brij S2 |

In the above composition, idebenone has a saturation concentration of 145 g/l at room temperature and of 103 g/l at 4° C.

The invention claimed is:

1. A transmucosal delivery system for idebenone, comprising an outer, hydrophilic, phase that makes up 20 to 70 wt. % of the total weight of the transmucosal delivery system for idebenone and which contains at least one hydrophilic polymer, and an inner, hydrophobic, phase which contains idebenone and at least one hydrophobic substance, wherein the at least one hydrophobic substance in the inner, hydrophobic, phase comprises methyl salicylate, tributyl citrate, triethyl citrate, eucalyptol, methyl salicylate, linoleic acid, oleic acid and/or mixtures thereof, wherein the inner, hydrophobic, phase is emulsified in the form of droplets in the outer phase, characterised in that the inner, hydrophobic, phase is stabilised by at least one emulsifier in the outer phase, wherein the at least one emulsifier comprises polysorbate, sorbitan esters, polyoxyethylene fatty acid ethers and/or mixtures thereof, and wherein the transmucosal delivery system for idebenone further comprises a vitamin E free-radical scavenger.

2. The transmucosal delivery system for idebenone according to claim 1, characterised in that idebenone is present substantially in the inner, hydrophobic, phase.

3. The transmucosal delivery system for idebenone according to claim 1, characterised in that idebenone is present dissolved in non-crystalline form.

4. The transmucosal delivery system for idebenone according to claim 1, characterised in that idebenone is present in a pharmaceutically effective concentration below its saturation concentration.

5. The transmucosal delivery system for idebenone according to claim 1, characterised in that the at least one hydrophilic polymer comprises polyvinyl alcohol, polyvinylpyrrolidone, a cellulose derivative and/or copolymers thereof.

6. The transmucosal delivery system for idebenone according to claim 1, characterised in that the at least one hydrophobic substance in the inner, hydrophobic, phase has a logP value of greater than about 1.

7. The transmucosal delivery system for idebenone according to claim 1, characterised in that the at least one emulsifier has an HLB value of 3 to 15.

8. The transmucosal delivery system for idebenone according to claim 1, characterised in that the inner phase makes up 30 to 60 wt. %, relative to the total weight of the transmucosal delivery system for idebenone.

9. The transmucosal delivery system for idebenone according to claim 1, characterised in that the emulsifier makes up 2 to 7 wt. %, relative to the total weight of the transmucosal delivery system for idebenone.

10. The transmucosal delivery system for idebenone according to claim 3, characterised in that idebenone is substantially in the inner, hydrophobic, phase.

11. The transmucosal delivery system for idebenone according to claim 4, characterised by a idebenone concentration which corresponds to 90% of the saturation concentration of idebenone in the at least one hydrophobic substance.

12. The transmucosal delivery system for idebenone according to claim 1, wherein the at least one hydrophobic substance comprises at least one of methyl salicylate and eucalyptol.

* * * * *